(12) United States Patent
Efinger et al.

(10) Patent No.: US 8,177,919 B2
(45) Date of Patent: May 15, 2012

(54) MEDICAL CLEANING DEVICE FOR CLEANING INTERIOR SURFACES OF HOLLOW SHAFTS

(75) Inventors: Andreas Efinger, Rietheim (DE); Horst Weiss, Muehlheim (DE)

(73) Assignee: Karl Storz GmbH & Co. KG (DE)

( * ) Notice: Subject to any disclaimer, the term of this patent is extended or adjusted under 35 U.S.C. 154(b) by 326 days.

(21) Appl. No.: 12/412,200

(22) Filed: Mar. 26, 2009

(65) Prior Publication Data

US 2009/0242001 A1 Oct. 1, 2009

(30) Foreign Application Priority Data

Mar. 26, 2008 (DE) .................. 10 2008 016 911

(51) Int. Cl.
*B08B 3/02* (2006.01)
(52) U.S. Cl. .................. 134/169 C; 134/166 C
(58) Field of Classification Search .............. 134/166 C, 134/168, 169 C, 170; 310/321–325
See application file for complete search history.

(56) References Cited

U.S. PATENT DOCUMENTS

| | | | | |
|---|---|---|---|---|
| 3,071,159 | A * | 1/1963 | Coraggioso | 138/38 |
| 3,698,408 | A * | 10/1972 | Jacke | 134/122 R |
| 4,977,900 | A | 12/1990 | Fehling et al. | |
| 5,240,675 | A * | 8/1993 | Wilk et al. | 422/22 |
| 5,810,155 | A * | 9/1998 | Hashimoto et al. | 198/630 |
| 5,830,127 | A * | 11/1998 | DeCastro | 600/157 |
| 5,885,133 | A * | 3/1999 | Williams, Jr. | 451/40 |
| 6,044,855 | A | 4/2000 | Mönch | |
| 6,626,235 | B1 * | 9/2003 | Christie | 165/158 |
| 6,892,738 | B2 * | 5/2005 | Bran et al. | 134/1.3 |
| 6,920,662 | B2 * | 7/2005 | Moore | 15/104.2 |
| 2006/0201670 | A1 * | 9/2006 | Stewart | 166/241.6 |

FOREIGN PATENT DOCUMENTS

| | | |
|---|---|---|
| DE | 280737 | 3/1913 |
| DE | 3710517 | 10/1988 |
| DE | 29620011 U1 | 1/1997 |
| DE | 19646584 | 4/1998 |
| DE | 29920599 | 5/2000 |
| DE | 10024133 DE | 11/2001 |
| DE | 102005048211 A1 | 4/2007 |
| GB | 2 299 599 | * 10/1996 |
| JP | 64-080484 | * 3/1989 |
| JP | 07-000935 | * 1/1995 |
| JP | 2005-160753 | * 6/2005 |
| RU | 724107 | * 3/1980 |
| RU | 1147459 | * 3/1995 |

OTHER PUBLICATIONS

European Search Report; EP 09 15 6211; Jul. 13, 2009; 5 pages.

* cited by examiner

*Primary Examiner* — Frankie L Stinson
(74) *Attorney, Agent, or Firm* — St. Onge Steward Johnston & Reens LLC

(57) ABSTRACT

A medical cleaning device is used to clean interior surfaces of hollow shafts of medical instruments. The device has a closed body which can be inserted into the hollow shaft of the medical instrument to be cleaned, an outer diameter of the body being smaller than a clear inner diameter of the hollow shaft such that an inner lumen remains which is reduced compared to the inner lumen of the hollow shaft. The body has a connection starting from one end, a cleaning liquid can be guided into the reduced inner lumen when the body is inserted in the hollow shaft. Furthermore, provision is made for a support by means of which the body can be supported on the medical instrument.

14 Claims, 6 Drawing Sheets

MEDICAL CLEANING DEVICE FOR CLEANING INTERIOR SURFACES OF HOLLOW SHAFTS

CROSS-REFERENCE TO RELATED APPLICATIONS

The present application claims priority of German patent application No. 10 2008 016 911.0 filed on Mar. 26, 2008.

FIELD OF THE INVENTION

The invention relates to a medical cleaning device for cleaning interior surfaces of hollow shafts of medical instruments.

BACKGROUND OF THE INVENTION

Medical instruments with hollow shafts are used in minimally-invasive medical engineering.

The hollow shaft of the medical instrument is inserted into the body through an incision, and appropriate manipulations are then undertaken in the body through the hollow shaft.

In the process, the inner surface of the hollow shafts is contaminated and has to be cleaned.

One step of a cleaning process consists of guiding a cleaning liquid through the hollow shaft in order to rinse away contamination or pollution adhering to the inner surface. The term cleaning liquid is also understood to include pure rinsing liquids which, for example, can also be provided to rinse remains of a liquid cleaning means, for example, from the inner surface.

Due to the fact that minimally-invasive surgery is widespread, it has become usual to carry out such cleaning and rinsing processes using appropriate machines. To this end, the hollow shafts have to be connected to a connection by means of which the hollow shaft is supplied with the cleaning or rinsing liquid. Since most hollow shafts have a very small clear inner diameter, the connections are provided with a relatively small cross section, for example with a diameter of 3.5 mm.

Cleaning hollow shafts with relatively large diameters, and hence with large lumens, poses problems. Said shafts sometimes also have cross-sectional shapes which differ from circular geometry.

Such medical instruments are, for example, devices to remove the vena saphena magna, that is to say the great saphenous vein, which runs along the lower leg and the thigh and up to the region of the groin. The great saphenous vein is often removed to use it as a transplant in coronary and vessel surgery.

The hollow shaft of this medical instrument has a length of approximately 45 cm and a clear inner diameter of 5 mm.

Operation bronchoscopes are also large-bore instruments, and likewise have lengths in the region of 40 cm and an inner diameter of up to 13 mm.

Cleaning such large-bore hollow shafts with current cleaning or rinsing machines having connections of the order of 3.5 mm cross-sectional diameter and having a rinsing pressure of 0.2 bar is problematic. This is because it is not possible to completely fill the lumen with the cleaning/rinsing liquid and hence ensure that the entire inner surface is sufficiently wetted with the cleaning/rinsing liquid.

The applicant has undertaken trials to the effect of introducing perforated hollow shafts provided with a number of lateral exit openings into the large-bore hollow shafts. The cleaning/rinsing liquid is inserted into the interior of this perforated hollow shaft and emerges radially through the numerous openings. Using this, the inner surface can be sprayed more or less evenly with the cleaning/rinsing liquid.

However, it was determined in practical use that even with this auxiliary construction, even application of the cleaning liquid on the inner surface of a large-bore hollow shaft cannot be ensured.

Therefore, the object of the present invention is to remedy this situation and provide a cleaning device by means of which the interior surface of hollow shafts, in particular of large-bore hollow shafts of medical instruments, can be cleaned or rinsed immaculately.

SUMMARY OF THE INVENTION

According to the invention, the object is achieved by a medical cleaning device by means of said device having a closed body which can be inserted into the hollow shaft of the medical instrument to be cleaned, an outer diameter of the body being smaller than a clear inner diameter of the hollow shaft such that an inner lumen remains which is reduced compared to an inner lumen of the hollow shaft, the body having a connection by means of which, starting from one end, a cleaning liquid can be guided into the reduced inner lumen when the body is inserted in the hollow shaft, and with a support by means of which the body can be supported on the medical instrument.

These measures now exhibit a number of advantages. One advantage lies in the fact that by inserting the closed body into the hollow shaft of the instrument to be cleaned, the lumen onto which the cleaning/rinsing liquid has to be applied is significantly reduced, specifically to the reduced inner lumen.

It is of course the object to clean the interior surface of the hollow shaft, for which purpose it suffices if a relatively thin liquid film runs over this surface, for example of the order of 0.3 to 2 mm. If a large-bore hollow shaft with an inner diameter of, for example, 15 mm is cleaned and is completely filled with cleaning/rinsing liquid that flows through it, the vast majority of liquid would in any case flow axially in the inner core of the hollow shaft lumen, without ever contacting the interior surface to be cleaned. This not only leads to large quantities of cleaning/rinsing liquid being required, but also leads to having to later dispose of a relatively large volume of contaminated quantities of cleaning/rinsing liquid.

The previously mentioned measure of inserting a closed body, which reduces the inner lumen to the reduced inner lumen, removes these disadvantages. Additionally, a higher flow velocity can be attained at an unchanging feed pressure if this reduced inner lumen is correspondingly small such that already the increased flow velocity can attain an additional cleaning effect to the effect that adhering contamination, for example blood, tissue or other particles, are dragged along. Hence, an increased cleaning effect can be attained using a smaller amount of cleaning/rinsing liquid.

The provision of a connection can connect the medical cleaning device to an appropriate cleaning/rinsing means line, after the device was inserted into the instrument to be cleaned.

The provision of a support, which can also be designed as a coupling, affords the possibility of supporting the cleaning device on the medical instrument in a precisely aligned manner. This ensures, for example, that a clearly defined space remains around the closed body inserted into the hollow shaft to be cleaned; the cleaning/rinsing liquid can flow through this space such that the liquid is guaranteed to be applied to the entire interior surface of the hollow shaft. The support or coupling can comprise, for example, screws, pins or a latching connection. This eases handling of the cleaning device or the assembly of cleaning device and shaft.

Hence, it is possible to also process large-bore hollow shafts in conventional cleaning/rinsing machines by creating the reduced free inner lumen by additionally inserting the medical cleaning device according to the invention, to be precise, but by nevertheless having the entire interior surface uncovered for the cleaning or rinsing process.

In a further refinement of the invention, the geometry of the body is selected such that the cross section of the reduced inner lumen is smaller than or equal to the cross section of the connection.

These conditions make it possible to ensure that the cleaning/rinsing liquid supplied via the connection or the cross section of the latter can occupy the entire reduced inner lumen such that no hollow spaces or air bubble spaces can be created, onto which the liquid is not applied. By the appropriate selection of the geometry, it is also possible to clean and rinse the most diverse large-bore hollow shafts in conventional, that is to say existing, machines with standardized connections, e.g. with 3.5 mm cross section.

In a further refinement of the invention, the body has flow-influencing elements on its outside.

The advantage of this measure is that the flow or the flow profile of the liquid through the reduced inner lumen can be influenced by these elements. These flow-influencing elements can, for example, impose a type of helical movement on the flow such that the liquid flow flows through the reduced inner lumen with such a movement characteristic, as a result of which certain cleaning and rinsing effects can be achieved. If the rinsing of liquid contamination is all that is desired, effecting a laminar flow can suffice. If sticky particles, such as pieces of tissue or the like, adhere to the interior surface of the hollow shaft to be cleaned, it can also be desirable to generate a turbulent flow in a very targeted manner by the flow-influencing elements in order to obtain additional cleaning effects or removal effects by the turbulent vortices. Hence, it is possible to completely individually target the field of use of the medical instrument.

In one refinement of the invention, the flow-influencing elements are in particular selected from projections, preferably fin-like or annular projections, helical projections, recesses, preferably annular or helical recesses, roughening on the outside of the body to be inserted into the hollow shaft.

By the provision of these different flow-influencing elements, it is possible to obtain a particular flow characteristic in a very targeted manner as a function of the use of the instrument, the geometry of the instrument and possible contamination, which flow characteristic is the most expedient characteristic for the cleaning and rinsing effect to be achieved in each case.

In a further refinement of the invention, the body is rod-shaped.

The advantage of this measure is that the body has a very simple design and can also easily be produced true to size and is easy to handle. The high dimensional accuracy affords the possibility of reducing for example a greatly reduced inner lumen for example from a cross-sectional radius of 15 mm to 2 mm, with it then being possible for the provided support to hold the body in precisely this alignment. Inserting a rod-shaped body into a hollow shaft is also a process which can be carried out easily.

In a further refinement of the invention, the length of the body can be changed by joining body sections.

The advantage of this measure is that the length of the body can be varied to match it to the different lengths of hollow shafts. It is usual in the medical field for the length of the hollow shafts to be selected depending on the body size of the patient to be treated, that is to say different lengths are used in children, adolescents and adults. Then, it is sufficient to provide a base body with the support and the connection at one end, and to increase, or correspondingly decrease, the length of the body by attaching further body sections at the opposite end. This also now provides the option of coupling body sections with different surface designs to one another such that it is possible for a change between laminar, turbulent or any other directed flow to be achieved again and again. This highlights the high flexibility of the device according to the invention compared to different cleaning/rinsing requirements.

In a further refinement of the invention, the cross-sectional geometry of the body corresponds to the cross-sectional geometry of the hollow shaft.

The vast majority of hollow shafts will have a circular cross section and so in this case the inserted rod-shaped body will also have a circular cross section. When the rod-shaped body is inserted, this results in an annularly reduced inner lumen with an unchanging geometry with respect to the thickness. If the hollow shaft is not circular but oval or has any other shape, the cross section of the body can then be shaped in accordance with the geometry such that a reduced inner lumen with an unchanging thickness is created throughout.

In a further refinement of the invention, the cleaning device has flow-influencing elements causing a turbulent flow of the cleaning liquid in the case of irregularly shaped hollow shafts which, as a result of being irregular, have inner surface regions on the body of the cleaning device which are hard to clean, said elements being present at least in the region of this inner surface region.

The significant advantage of this measure is that, in the case of irregularly shaped hollow shafts and the possibly connected inner surface regions which are hard to clean, vortices can be obtained in a targeted manner in order to be able to securely detach adhering contaminations, even in this critical region. This again highlights the high adaptability and also individuality of the device toward hollow shafts which are problematic to clean.

In a further refinement of the invention, the body is composed of a flexible material such that it can also be inserted into a curved hollow shaft.

The advantage of this measure is that it is also possible to clean and rinse curved large-bore hollow shafts with excellent results by using the device according to the invention. This refinement is also advantageous in conjunction with angled shafts and those shafts whose cross section changes axially.

In a further refinement of the invention, the body composed of a flexible material has guide elements on its outside, which elements ease insertion and positioning of the body in the curved hollow shaft.

The advantage of this measure is that the guide elements not only ease the pushing in and pulling out of the body composed of flexible material into/out of the hollow shaft to be cleaned, but at the same time also ensure that the body can be spaced evenly from the inner surface to be cleaned such that again a relatively regular, reduced inner lumen is created throughout. These guide elements also ensure exact positioning in the case of straight shafts.

In a further refinement of the invention, at least one opening is present on the body in the region of the connection, by means of which opening the cleaning or rinsing liquid flows into the reduced inner lumen.

The advantage of this measure is that the liquid supplied by the connection can flow into the reduced inner lumen in a defined manner by means of this opening, can be distributed evenly there and can flow evenly distributed through the hollow shaft from the one side, on which the connection is arranged, to the opposite exit side for the liquid.

It is understood that the features which were mentioned above and will be explained below can be used not only in the respectively specified combinations, but also in any other combination or on their own, without departing from the scope of the present invention.

BRIEF DESCRIPTION OF THE DRAWINGS

Exemplary embodiments of the invention will be explained and described in more detail below with reference to the appended drawings, in which.

DETAILED DESCRIPTION OF THE INVENTION

A first exemplary embodiment of a medical cleaning device according to the invention illustrated in FIGS. 1 to 8 is in its entirety referred to by the reference number 10.

Figures 1, 2:
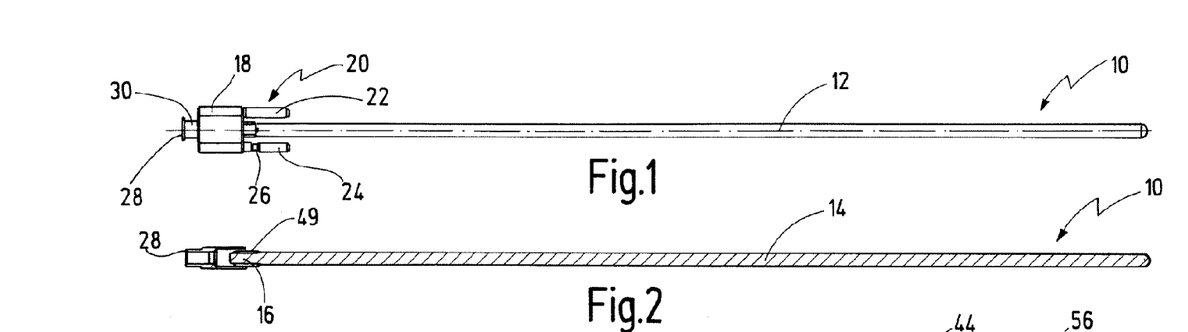
FIG. 1 shows a plan view of a first exemplary embodiment of a medical cleaning device.
FIG. 2 shows a longitudinal section of the device in accordance with FIG. 1, rotated by 90° about the longitudinal axis.

As can be seen particularly in FIGS. 1 and 2, the device 10 has an elongate body 12 in the form of a solid rod 14, in this case composed of steel. At one end 16, the rod is connected to a housing 18. The housing 18 has a support 20, the functionality of which is intended to be described later in conjunction with FIGS. 7 and 8.

The support 20 has two pins 22 and 24 protruding from the housing 18, which pins extend on both sides of the rod 14 and parallel to and at a distance from the latter. A peripheral, annular groove 26 is provided on the pin 24.

Figures 4, 5, 6:
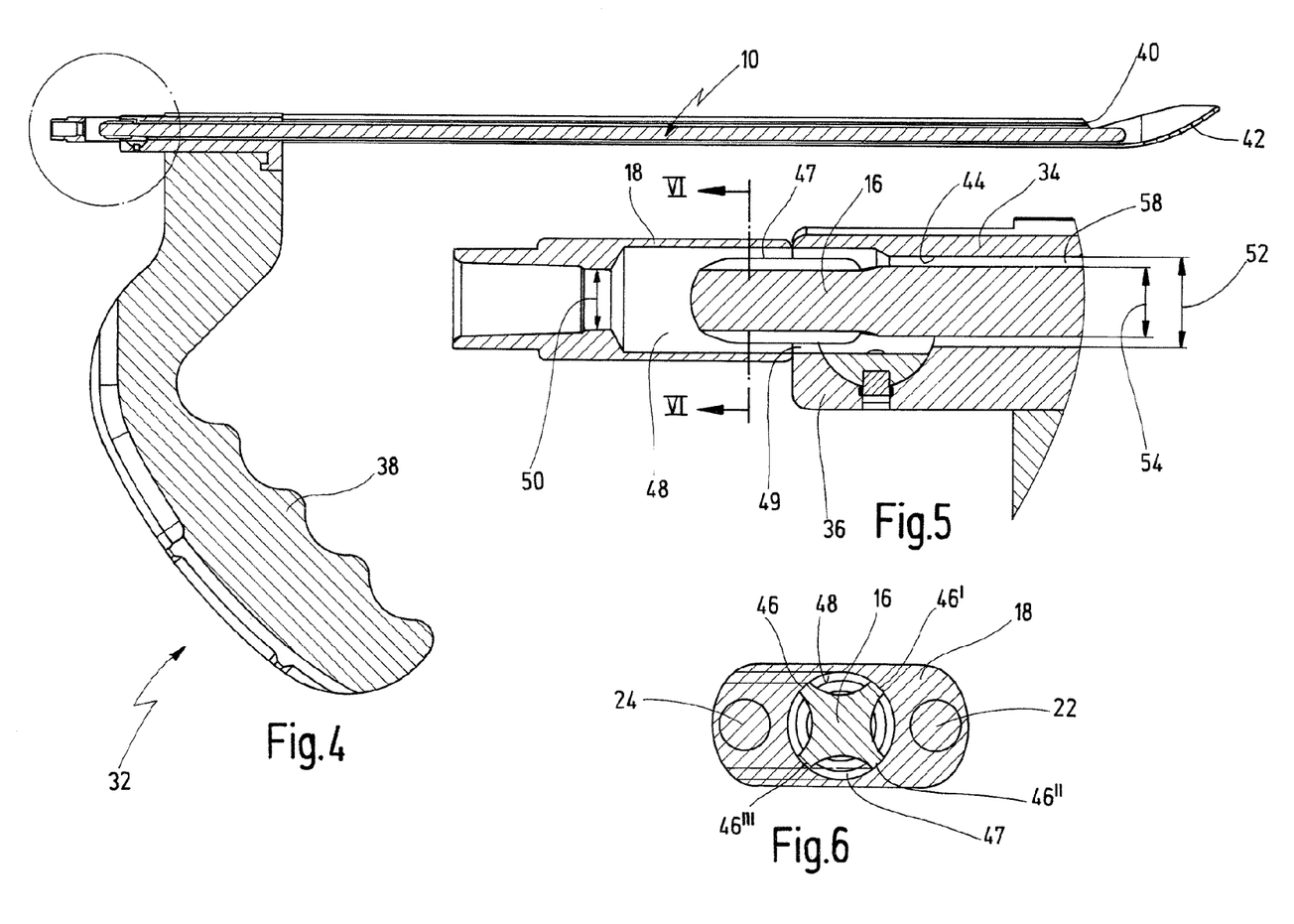
FIG. 4 shows a sectional illustration comparable to FIG. 3 with the cleaning device from FIG. 2 inserted into the hollow shaft.
FIG. 5 shows a greatly enlarged sectional illustration of the region delimited in FIG. 4 by means of a circle.
FIG. 6 shows a section along the line VI-VI in FIG. 5.

A connection 28 is provided at the proximal end of the housing 18 and it is designed as a so-called Luer connection 30. A Luer connection 30 is a standardized connection in the medical sector, to which a correspondingly shaped connection of a liquid line, for example, can be connected by means of a 90° rotation. As can be seen in the sectional illustration of FIG. 2, the housing 18 is hollow in the interior and connected to the connection 28. The rod 14 extends into the housing 18, that is to say it extends into the inner bore 48, as shown on the left-hand side of FIG. 5. FIG. 6 shows that this back end 16 of the rod 14 has four webs 46, 46', 46" and 46"', by means of which this end is supported on the inner side of the housing 18 and hence connected to the latter. Hence there are openings between the webs 46, 46', 46" and 46"', with only the opening 47 indicated in this case, through which a liquid supplied to the housing 18 by the connection 28 can pass through.

Figure 3:
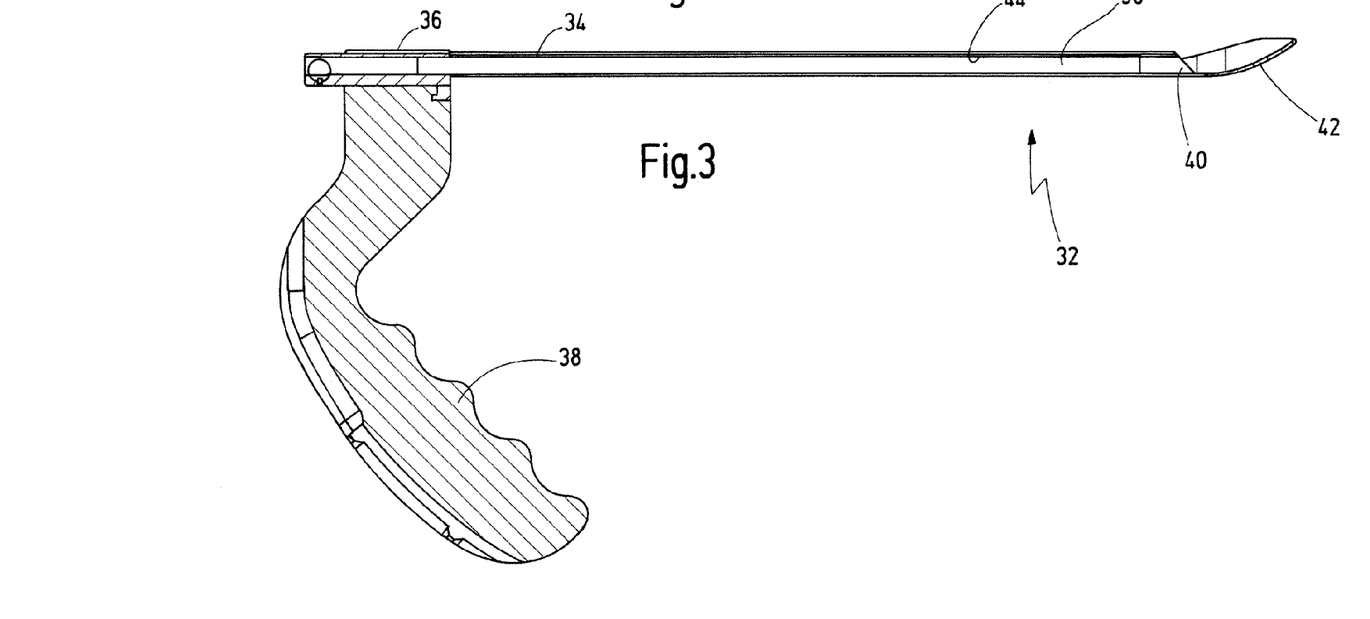
FIG. 3 shows a longitudinal section of a medical instrument, specifically a device for removing the great saphenous vein, the hollow shaft of which instrument is intended to be cleaned.

The device 10 according to the invention serves to be used in conjunction with a medical instrument 32, as illustrated in FIG. 3 in the longitudinal section. The medical instrument 32 is a device for removing the great saphenous vein from the leg of an adult human. The medical instrument 32 has an elongate hollow shaft 34, the length of which is approximately 45 cm and the clear inner diameter of which is approximately 5 mm. The hollow shaft is connected to a handle 38 at the proximal end 36; at the distal end 40, provision is made for a spatula tip 42.

The hollow shaft 34 has an inner surface 44 which is intended to be cleaned and rinsed after use, that is to say after the removal of the vein from the leg.

To this end, the device 10 is inserted into the proximal open end 36 of the hollow shaft 34.

Figures 7, 8:
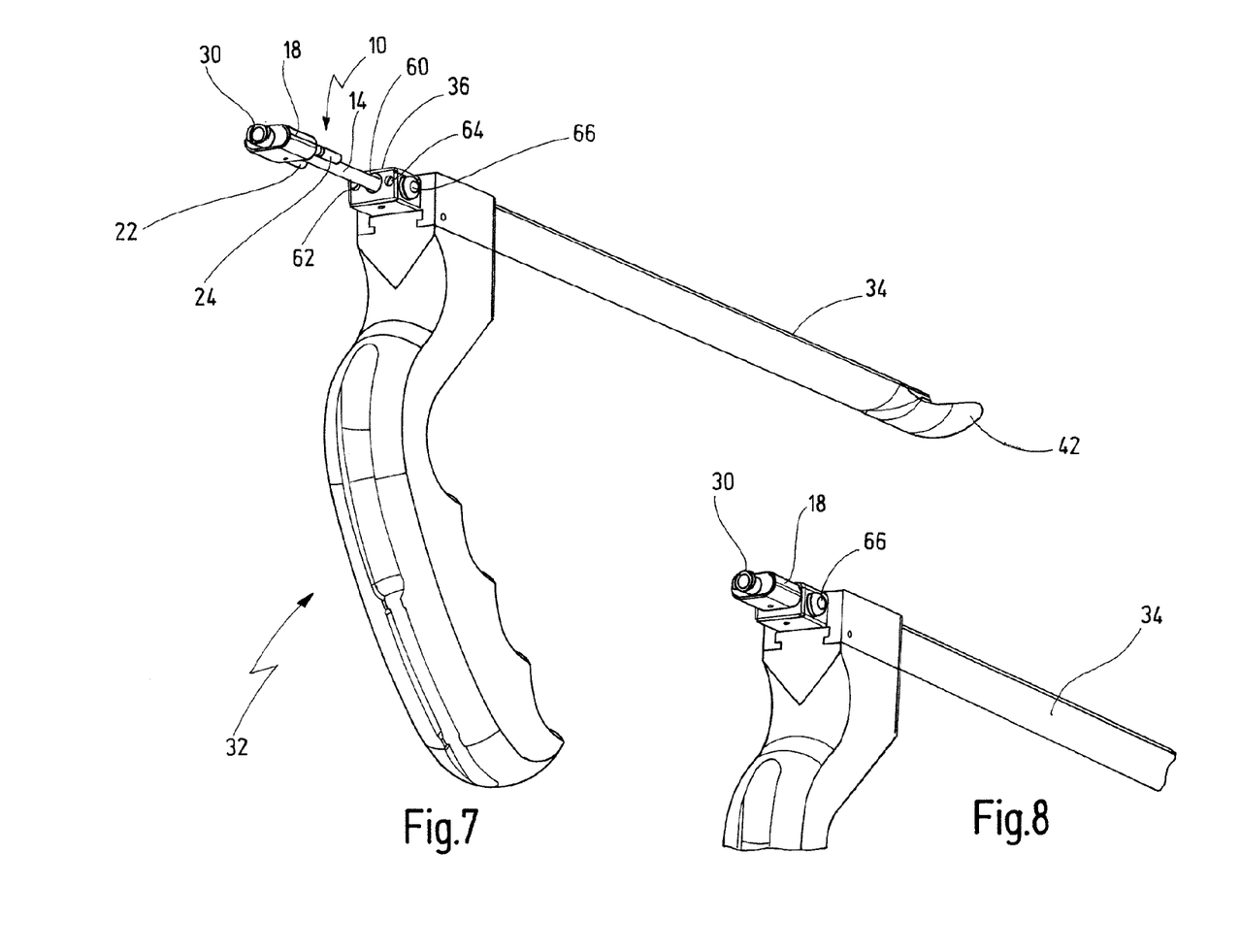
FIG. 7 shows a perspective view of the medical instrument of FIG. 3, in which the device of FIG. 1 is just being inserted into the hollow shaft.
FIG. 8 shows a sectional illustration comparable to the illustration of FIG. 7 with a medical cleaning device which has completely been inserted into the hollow shaft.

FIG. 7 illustrates a situation in which the rod 14 of the device 10 has already to a large part been inserted through an opening 60 at the proximal end 36 of the hollow shaft 34. At this proximal end, two further openings 62 and 64 are provided on both sides of the opening 60 which are used for affording the possibility of inserting the projecting pins 22 and 24 of the support 20 into them. A transversely protruding, spring-loaded locking pin 66 is provided on that side on which the pin 24 provided with the annular groove is inserted.

Once the device 10 has been completely inserted into the hollow shaft 34, the two pins 22 and 24 have entered the corresponding openings 62 and 64 and the locking pin 66 has latched in the annular groove 26 of the pin 24. This final position is illustrated in FIG. 8.

The sectional illustration of FIG. 5 shows that the distal end of the housing 18 in this case lies flush with and terminates in a sealing manner at the proximal end 36 of the medical instrument 32.

The sectional illustration of FIG. 5 also shows that the outer diameter 54 of the rod 14 is less than the clear inner diameter 52 of the hollow shaft 34. Hence, the inner lumen 56 of the hollow shaft 34 (see FIG. 3) was reduced to a reduced inner lumen 58.

In this case, the dimensions are selected such that the cross section of the inner lumen 58 at most equals or is smaller than the cross section 50 of the Luer connection 30.

This ensures that a liquid supplied by the Luer connection 30 completely fills the inner lumen 58 of the now remaining annular space. Liquid is applied to the entire inner surface 44 of the hollow shaft 34 to be cleaned and possible contaminations are rinsed away or dragged along and are guided to the distal end 40 of the medical instrument 32 and there they are led away in the region of the spatula tip 42. The support 20 ensures that the device 10 is held in a captive and secure manner on the medical instrument 32 during the cleaning and rinsing process, to be precise with a particular geometric outside, which leads to the geometrically exact, regular, annularly shaped reduced inner lumen 58.

In the state shown in FIG. 8, the assembly can, for example, be placed into a cleaning and rinsing machine. A rinsing or cleaning liquid line is connected to the Luer connection 30, and the further process can then be carried out in an automated fashion.

Once the process is finished, the locking pin 66 is moved to the side and the device 10 can again be pulled away from the hollow shaft 34.

Figure 9:
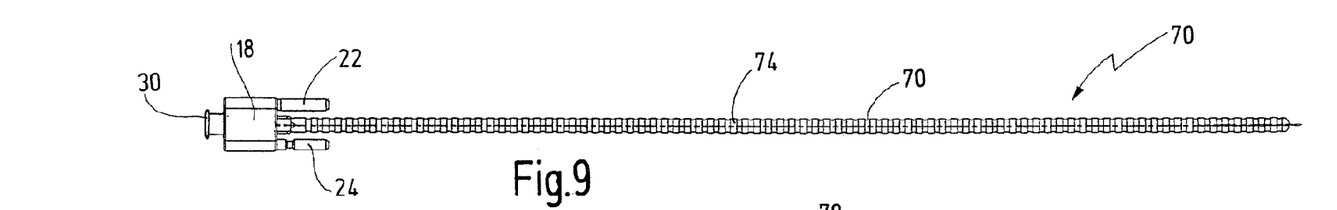
FIG. 9 shows an illustration comparable to the illustration of FIG. 1 of a second exemplary embodiment with recesses in the rod-shaped body.
Figures 10, 11:
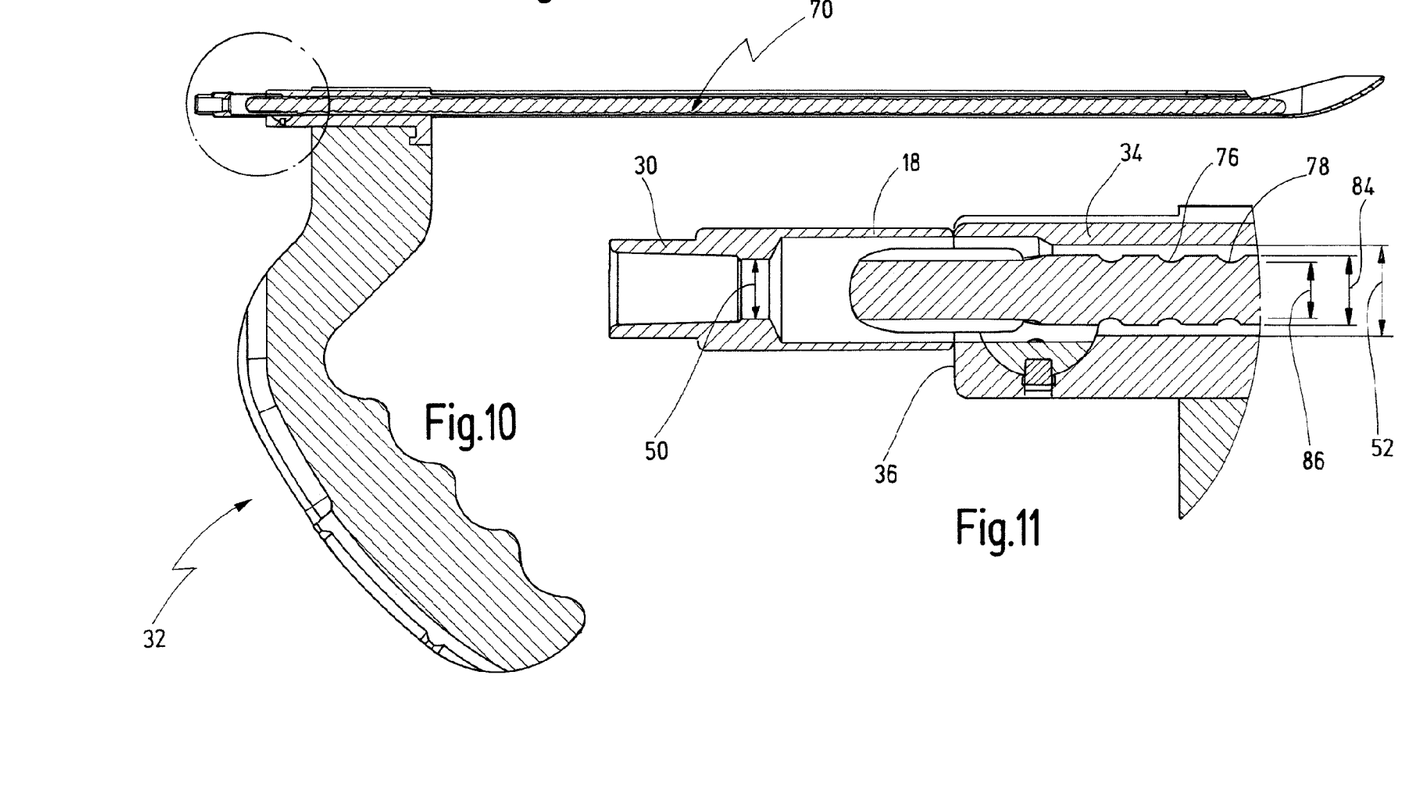
FIG. 10 shows an illustration comparable to the illustration of FIG. 4, in which the medical cleaning device in accordance with FIG. 9 is inserted into the hollow shaft of the instrument in accordance with FIG. 3.
FIG. 11 shows an enlarged illustration corresponding to the illustration of FIG. 5 of the region in FIG. 10 delimited by a circle.

FIGS. 9 to 11 illustrate a second exemplary embodiment of a device 70 according to the invention, which differs from the previously described device 10 solely by the fact that the rod 74 has recesses 76 in the form of annular notches 78. Otherwise, the device 70 has the same design as the device 10, therefore the same reference symbols are also used for these components. This means that in this case there is also a housing 18 provided with a Luer connection 30 at one end. The support again consists of the two protruding pins 22 and 24.

FIGS. 10 and 11 illustrate how the device 70 is inserted into the previously described medical instrument 32, specifically the device for removing a great saphenous vein.

The sectional illustration of FIG. 11 shows that the design of the housing 18 and the resting on the proximal end 36 of the medical instrument are shaped in the same manner, only the rod 74 has the described notches 78. Here too, the outer diameter 84 of the rod 74 is again smaller than the clear inner diameter 52 of the hollow rod 34 such that here again too a reduced inner lumen, not designated in any more detail, is created. This inner lumen is only slightly enlarged to the effect that the liquid also has to fill the space of the annular notches 78 since the floor diameter 86 is even slightly smaller than the outer diameter 84.

The provision of these notches 78 makes it possible to generate turbulent flows, that is to say corresponding vortices, in order to increase the cleaning or rinsing effect.

Figure 12:
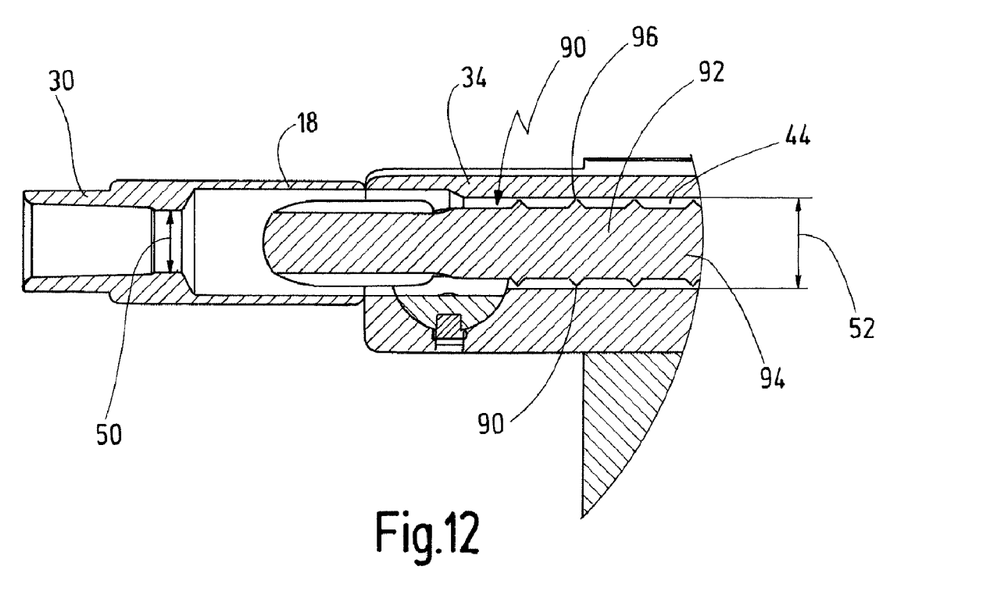
FIG. 12 shows an illustration of a third exemplary embodiment, comparable to the illustrations of FIGS. 5 and 11, in which the outside of the rod-shaped body is provided with projections.

In the third exemplary embodiment of a device 90 according to the invention shown in FIG. 12, a body 92 in the form of a rod 94 is present again, and the outside of said rod has protruding projections 96.

Otherwise, the device 90 is designed like the previously described devices 10 or 70, that is to say, once again a housing 18 is present which merges into a Luer connection 30. The outer diameter of the rod 94 is then again slightly smaller than the clear inner diameter 52 of the hollow shaft 34 of the medical instrument. If the projections 96 are designed as annularly peripheral projections, the tip of the projection 96 is at a certain distance from the inner surface 44 such that liquid can pass through.

The projections can also be designed in the form of a helical male screw. Significant turbulence occurs in the region of the projections 96, which facilitates additional rinsing of in particular sticky or slimy contaminations.

Figure 13:
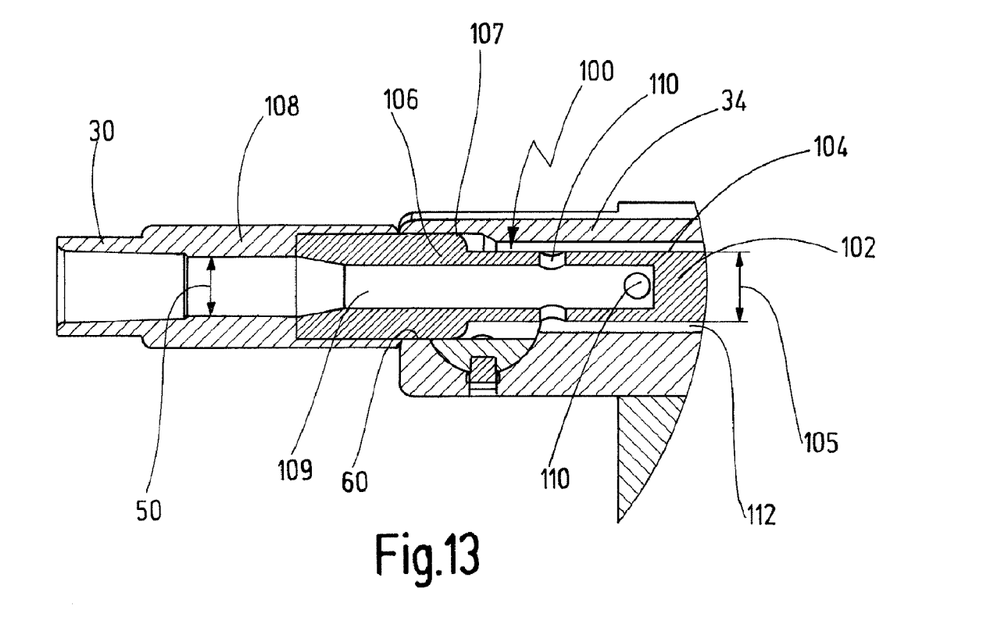
FIG. 13 shows an illustration comparable to the illustration of FIG. 12 of a fourth exemplary embodiment.

FIG. 13 illustrates a fourth exemplary embodiment of a device 100 according to the invention. In this case too, an elongate, closed, solid body 102 is present which has the form of a rod 104, which is smooth on its outside, and the diameter 105 of which once again is slightly smaller than the clear inner diameter of the hollow shaft 34 of the instrument.

In contrast to the previously shown exemplary embodiments, the support 106 is in this case designed as a type of plug 107 which can be inserted directly into an end of the corresponding hollow shaft 34. Additionally, the material in this region is designed in a more or less flexible manner. The connection 108 is then placed onto the outer end of the plug 107. The plug 107 ensures a liquid-tight termination.

It is for this reason that an axial, central bore 109 is present and connected to openings 110.

The openings 110 are positioned such that they merge into the reduced inner lumen 112.

That is to say if the device 100 is inserted into a medical instrument 32, a liquid is guided into the reduced inner lumen 112 via the connection 108, the inner bore 109 in the plug and the lateral openings 110.

To this end, provision is also made here for the outer diameter 105 of the rod 104 to again be less than the clear inner diameter of the hollow shaft 34 to be cleaned.

Figures 14, 15:
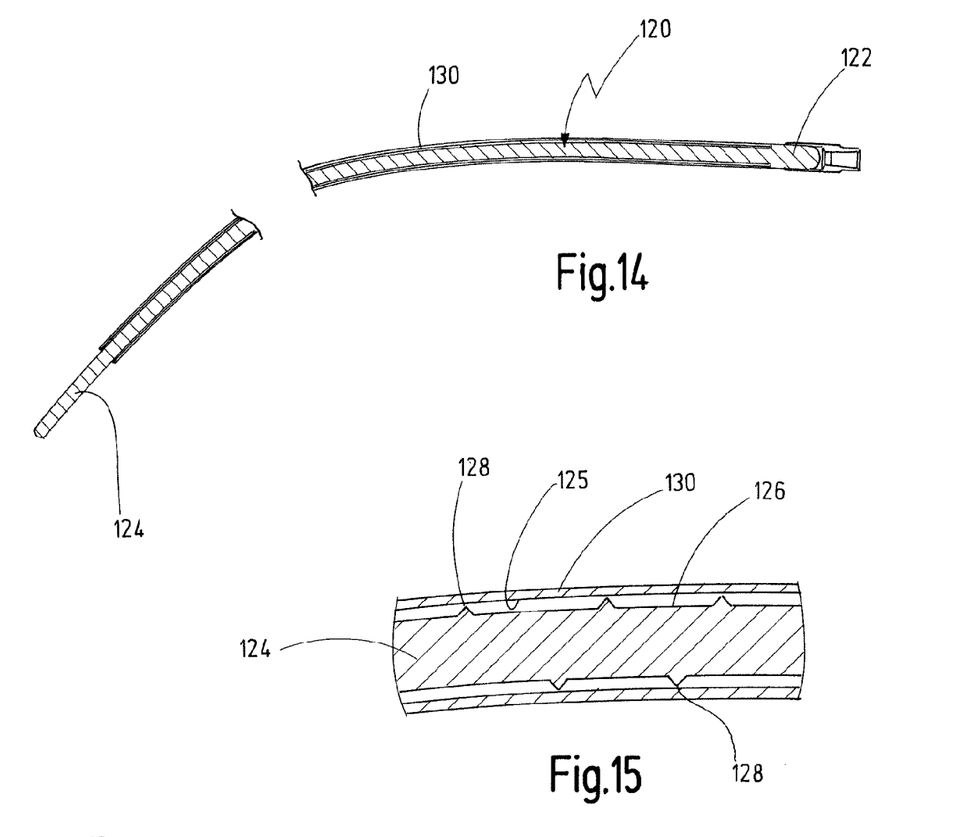
FIG. 14 shows a fifth exemplary embodiment of a medical cleaning device with a rod-shaped body composed of a flexible material and which is inserted in a curved hollow shaft.
FIG. 15 shows an illustration of FIG. 14 greatly enlarged, in sections, in which projections can be seen to be present on the outside.

In a further, fifth example of a device 120 according to the invention illustrated in FIGS. 14 and 15, the device has a body 122 of flexible or ductile material.

In this case, the body 122 is also designed as a rod 124 extending in the longitudinal direction, at the outside 126 of which guide elements 128 in the form of projections 129 protrude. As a result of this refinement, the device 120 can easily be inserted into a curved hollow shaft 130. The guide elements 128 ensure that the body 122 lies evenly spaced from the inner surface 125 of the hollow shaft 130 to be cleaned, even in the curved hollow shaft 130.

These guide elements 128 additionally have the effect, as described in the exemplary embodiment in conjunction with FIG. 12, that is to say that corresponding turbulence can be effected in the region of the projections. However, in this case the protrusions lie against the inner side of the surface 125 in punctiform fashion for the purposes of support.

Figure 16:
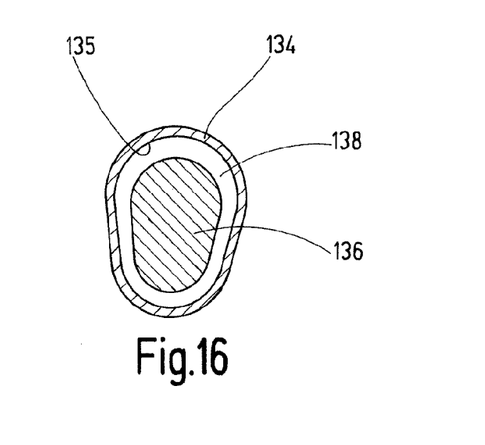
FIG. 16 shows a cross section through an instrument which does not have a round hollow shaft and a correspondingly shaped, rod-shaped body inserted therein.

FIG. 16 shows a sixth exemplary embodiment, in which a hollow shaft 134 is illustrated which is not shaped like a circle, but rather like an oval with a curved side which is smaller. In this case, the body 136 of the corresponding device according to the invention is designed with a similar geometry, but is slightly smaller in its dimensions such that once again the reduced inner lumen 138 is created when the body 136 is inserted into the hollow shaft 134 of the instrument to be cleaned. In this case, it is also possible for the inner surface 135 to be cleaned with good results.

Figure 17:
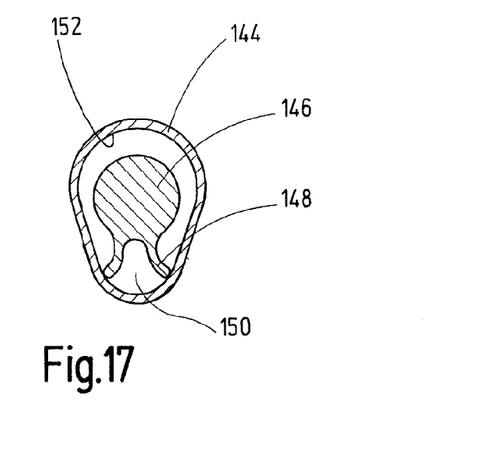
FIG. 17 shows an illustration comparable to FIG. 16, in which the inserted rod-shaped body of the cleaning device additionally has guide elements.

The seventh exemplary embodiment illustrated in FIG. 17 has a hollow shaft 144 which has a similar shape to that of the exemplary embodiment of FIG. 16; however, the body 146 of the device according to the invention inserted into the hollow shaft 144 is rod-shaped in this case with an approximately circular cross section. Guide elements 148 project from the outside, which ensure appropriate turbulence or vortices in the possibly critical, that is to say difficult to clean, inner surface region 150. Hence, in this case it is also ensured that the entire inner surface 152 can be cleaned with outstanding results.

The invention claimed is:

1. A medical cleaning device for cleaning an interior surface of a hollow shaft of a medical instrument, comprising
 a closed body which can be inserted into said hollow shaft of said medical instrument, an outer diameter of said closed body being smaller than a clear inner diameter of said hollow shaft such that an inner lumen remains between an inner surface of said hollow shaft and an outer surface of said closed body, said inner lumen being reduced compared to a free inner lumen of said hollow shaft, said closed body having a connection via which a cleaning liquid can be guided into said inner lumen when said closed body is inserted in said hollow shaft, said cleaning liquid being guided into said reduced inner lumen from one end thereof, and a housing connected to said closed body at one end of said closed body, said housing having a support for supporting said closed body on said medical instrument, said support having at least one projection protruding from said housing, said at least one projection being provided for entering into at least one corresponding opening provided at said medical instrument to be cleaned, said support holding said inserted closed body in a precisely aligned manner.

2. The medical cleaning device of claim 1, wherein a geometry of said closed body is selected such that a cross section of said reduced inner lumen being equal or smaller than a cross section of flow of said cleaning liquid flowing through said connection.

3. The medical cleaning device of claim 1, wherein said closed body has flow-influencing means on its outside.

4. The medical cleaning device of claim 3, wherein said flow-influencing means are selected from the group consisting of projections, recesses, roughening.

5. The medical cleaning device of claim 4, wherein said projections are selected from the group consisting of fin-like projections, annular projections and helical projections.

6. The medical cleaning device of claim 4, wherein said recesses are selected from annular and helical recesses.

7. The medical cleaning device of claim 1, wherein said closed body is a rod-shaped body.

8. The medical cleaning device of claim 1, wherein a length of said closed body can be changed by joining body sections to said closed body.

9. The medical cleaning device of claim 1, wherein a geometry of a cross section of said body corresponds to a geometry of a cross section of said hollow shaft.

10. The medical cleaning device of claim 1, wherein said hollow shaft has an irregularly shape, sections of said irregular shape being difficult to clean due to said irregular shape, and wherein said closed body has flow-influencing elements causing a turbulent flow of cleaning liquid in said sections of irregular shape.

11. The medical cleaning device of claim 1, wherein said closed body being composed of a flexible material such that it can be also inserted into a curved hollow shaft.

12. The medical cleaning device of claim 11, wherein said closed body of flexible material has guide elements provided on an outside thereof, said guide elements ease an insertion and a positioning of said closed body in said curved hollow shaft.

13. The medical cleaning device of claim 1, wherein at least one opening is present on said closed body in a region of said connection via which at least one opening said cleaning liquid flow from said connection into said reduced inner lumen.

14. The medical instrument of claim 1, wherein said support is designed as a coupling.

* * * * *